(12) United States Patent
Frater et al.

(10) Patent No.: US 6,951,964 B2
(45) Date of Patent: Oct. 4, 2005

(54) METHOD FOR PRODUCING MACROCYCLIC KETONES

(75) Inventors: Georg Frater, Winterthur (CH); Matthias Nagel, Hermetschwil (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/469,177

(22) PCT Filed: Feb. 15, 2002

(86) PCT No.: PCT/EP02/01644
§ 371 (c)(1),
(2), (4) Date: Aug. 22, 2003

(87) PCT Pub. No.: WO02/068372
PCT Pub. Date: Sep. 6, 2002

(65) Prior Publication Data
US 2004/0082816 A1 Apr. 29, 2004

(30) Foreign Application Priority Data
Feb. 22, 2001 (EP) .............................. 01103613

(51) Int. Cl.[7] .......................... C07C 45/00; C07C 35/20; C07C 35/18
(52) U.S. Cl. ....................... 568/341; 568/375; 568/377; 568/821; 568/823
(58) Field of Search ............................... 568/341, 375, 568/377, 821, 823

(56) References Cited

FOREIGN PATENT DOCUMENTS

EP     0 955 285 A1    11/1999   ........... C07C/45/51
EP     1 236 707 A1     9/2002   ........... C07C/45/51

OTHER PUBLICATIONS

Taguchi et al. A Facile Route to d,I–Muscone. Tetrahedron Letters, No. 30, 1976, p 2617–2620.*
PCT/EP02/01644 Search Report dated Jun. 3, 2002.
PCT Written Opinion dated Jul. 09, 2002.
XP –000999992, Some Derivatives of Cyclododecane. Abstract Thermal Rearrangements of cis, and trans–1–Trimethylsilozy–1–vinylcyclodec–3–ene. Ring Strain Effects for the Siloxy–Cope Rearrangement. Tetrahedron Letters No. 7, pp. 513–516, 1970. CXY–Cope Rearrangements of Medium–Sized Rings.
Tetrahedron Letters 39 (1998) 333–334 Total Sythesis of the Naturally Occurring Furanoid Fatty Acid, $F_5$.
XP–000999994 Selective Reductive Cleavage of the Propargyl Oxygen Bond of Acetylenic Epoxides, A General Synthesis of 2–Ethynylcycloalkanones.
XP–000999980 299 Synthesen und thermolysen von 1–Alkinyl–2–methyl–1,2–epoxy–cycloalkanen[1]).—Versuche zur Ringerweiterung um drei Kohlenstoffatome.

Database Crossfire [Online]; Beilstein; Beilstein Registry No. 2440894; Jul. 5, 1989 (Jul. 5, 1989); XP002168440; * Zusammenfassung* & Khim. Geterotsikl. Soedin., Bd. 8, 1972, Seite 170.
XP002177204. Synthesis of 1 (3–hydroxypropynyl)–1–cyclododecanol and its cyclisation to bicycle [10,3,0]pentadec–1 (12–en–13–one. Chem. Abstracts vol. 96 No. 21 (1982).
XP002177205. Synthesis of 1–ethynylcyclododencanol and its isomerisation on a vanadium catalyst. Chem. Abstracts vol. 112, No. 9 (1990).

* cited by examiner

*Primary Examiner*—Johann Richter
*Assistant Examiner*—Sikarl A. Witherspoon
(74) *Attorney, Agent, or Firm*—Norris McLaughlin & Marcus PA

(57) ABSTRACT

The present invention relates to a novel thermo-isomerization method for rapidly and simply producing macrocyclic ketones of the formula Ia or Ib.

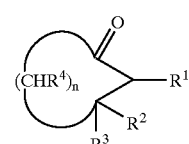

Ia

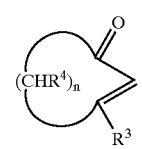

Ib

The macrocyclic ketones are prepared in the gas phase at temperatures above 500° C. rapidly and in a simple manner from alcohols of the formula IIa and IIb directly with a high yield.

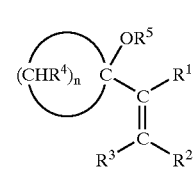

IIa

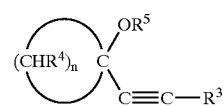

IIb

In the formulae Ia, Ib, IIa and IIb, R1–R5, and n have the meanings given in the description.

11 Claims, No Drawings

METHOD FOR PRODUCING MACROCYCLIC KETONES

The present invention relates to a novel thermo-isomerization method for rapidly and simply producing macrocyclic ketones.

Macrocyclic ketones are of considerable importance in perfumery because of their musk-like odor properties. In this connection, cyclopentadecanone (Exalton®), 3-methylcyclopentadecanone (muscone), cycloheptadec-9-en-1-one (civettone) and (E/Z)-cyclohexadec-5-en-1-one (Ambretone®, Musk TM II®) in particular are to date of commercial importance as musk ketones. As is known from the specialist literature, such macrocyclic ketones can be prepared by multistage syntheses which are essentially based on two basic methods:

a) Macrocyclization reactions (for example, the so-called acyloin condensation of α,ω-diesters with subsequent reduction or the intramolecular olefin metathesis (ring closure metathesis, RCM) etc.). Since polymerization processes should be avoided, most macrocyclization reactions are only carried out using high dilutions and are therefore too cost-intensive for reactions on an industrial scale.

b) Ring expansion reactions which are based either on a multistage sequence of anellation and fragmentation reactions, or on sigmatropic [3.3]-rearrangement reactions (e.g. oxy-Cope reaction of 1,2-divinylcycloalkan-1-ols), or also [1.3]-displacement reactions in the case of 1-vinylcycloalk-3-en-1-ols (W. Thies, P. Daruwala, *J. Org. Chem.* 1987, 52, 3798–3806).

Ring expansion reactions by 2 carbon atoms according to the principle of a [1.3]-displacement reaction are described in numerous scientific articles (for example in *Tetrahedron Lett.* 1970, 513–516). In the case of 1-vinyl-cyloalk-3-en-1-ols with a nine- to thirteen-membered ring system and endocyclic, homoallylic double bond in position 3, instead of [3.3]-rearrangement products (ring expansion by four carbon atoms), ring expansions in the sense of a [1.3]-displacement (ring expansion by two carbon atoms) was preferentially observed under the thermal conditions for oxy-Cope rearrangements. The yield is at most 25% since the elimination of water occurs as an undesired reaction. Significantly better yields (50–80%) are described when the vinyl alcohol has been converted into the corresponding trimethylsilyl ether prior to heating. The same products were obtained when the rearrangement reaction was carried out with the corresponding doubly unsaturated potassium alkoxide under strongly anionic conditions (2 mol equivalent of potassium hydride in HMPA at 25–100° C.).

In *J. Am. Chem. Soc.* 1974, 964, 200–203, it is expressly pointed out that both in the case of the trimethylsilyl ether derivative, and particularly also in the case of the non-derivatized vinyl alcohol itself, an analogous [1.3]-displacement reaction could no longer be observed at temperatures up to 320° C. as soon as the homoallylic endocyclic double bond (in position 3) was removed. The application of additionally forced reaction conditions (reaction temperatures up to 420° C.) led in both cases primarily to the formation of alkenes (elimination of water). *J. Chem. Soc.* 1978, 43, 1050–1057, describes that no products of a ring expansion could be observed with the use of anionic rearrangement conditions either, i.e. by treating the vinyl alcohol, which has a saturated ring system, with potassium hydride in HMPA for 4 or 24 h at room temperature.

The 1-vinylcyclopropanols, which are structurally related to the vinylcyclopropanes, rearrange irreversibly to give 2-substituted cyclobutanones when heated to only 100° C. within a short time with a [1.2]-migration. However, if, on the other hand, instead of the vinylcyclopropanols, their trimethylsilyl ether derivatives (1-trimethylsilyloxy-1-vinylcyclopropanes) are heated, then these can again be converted into cyclopentanones with a [1.3]-migration (*J. Am. Chem. Soc.* 1973, 95, 5311–5321; and *J. Org. Chem.* 1981, 46, 506–509).

*J. Org. Chem.* 1978, 43, 4903–4905 and *J. Org. Chem,* 1980, 45, 2460–2468 describe ring expansion by two carbon atoms also in the case of specially functionalized macrocyclic dithiaspiroketone derivatives (e.g. 1.5-dithiaspiro[5.12] octa-decan-7-one). This described method cannot be used on relatively small ring systems, such as on cyclododecanone as starting material.

An object of the present invention is a simple and cost-effective method for producing macrocyclic ketones.

Surprisingly, it has been found that, through the thermo-isomerization method according to the invention, macrocyclic ketones of the formula Ia or Ib can be produced in the gas phase at temperatures above 500° C. rapidly and in a simple manner directly with a high yield.

Accordingly, the invention provides in one of its aspects a thermo-isomerization method for producing macrocyclic ketones of the formula Ia and Ib

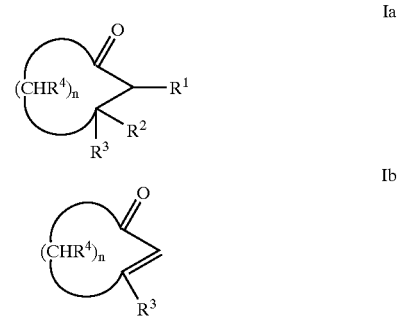

wherein
$R^1$, $R^2$ and $R^3$ are independently hydrogen or a $C_1$ to $C_6$ alkyl group,
$R^4$ is hydrogen, a linear or branched $C_1$ to $C_4$-alkyl group,
n is an integer of 7 to 14, and
in formula Ia, $R^1$ and $R^2$ or $R^2$ and $R^3$ can, independently of one another, form a ring.

The ketones of the formula Ia or Ib ring-extended by two carbon atoms are produced by converting under reduced pressure at 100–300° C. into the gas phase a macrocyclic tertiary allyl or propargyl alcohol of the formula IIa or IIb

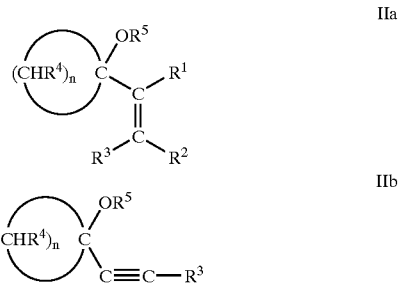

wherein $R^1$, $R^2$, $R^3$, $R^4$, and n have the same meanings as above, and $R^5$ is either hydrogen, trialkylsilyl, or an alkali metal cation, and then heating the macrocyclic tertiary allyl or propargyl alcohol of the formula IIa or IIb, converted into the gas phase, at temperatures of 500 to 700° C., and hydrolysis of the trialkyl silyl ether into the corresponding ketone of the formula Ia or Ib, if $R^5$ is a trialkylsilyl.

The size of the ring system is therefore described by n. If n=7, 10-membered cyclic ketones are obtained from 8-membered cyclic alcohols. In the case of n=14, 17-membered cyclic ketones can accordingly be obtained from 15-membered cyclic alcohols.

$C_1$–$C_6$ Alkyl is, for example, methyl, ethyl, propyl, isopropyl, butyl, sec- or tert-butyl, pentyl or hexyl, where methyl is particularly preferred.

Depending on the nature of the substituents on the vinyl group of the tertiary cyclic alcohol of the formula IIa used as starting material, thus the substituents are not hydrogen, the described method allows the simultaneous production of ring-expanded and additionally regioselective substituted macrocyclic ketones. The positions of the substituents in the macrocyclic ketones are located as shown in formula Ia on the two successive carbon atoms adjacent to the carbon atom of the carbonyl group (regarded as C(1)) and distribute themselves in the following way: $R^1$ is on the carbon atom directly adjacent to the carbonyl group (thus in the α-position) on C(2) and both $R^2$ and $R^3$ are each on the same ring half of the macrocyclic ketone at a distance of two carbon atoms from the carbonyl group (thus in the β-position) on C(3), directly adjacent to C(2). If, in the method described, instead of tertiary cyclic allyl alcohols, corresponding macrocyclic propargyl alcohols of the formula IIb are used, then macrocyclic ketones are obtained, which contain a double bond in direct conjugation to the carbonyl group (α,β-unsaturated ketones). If there is an additional substituent $R^4$ on the ring system of the cyclic alcohol (thus $R^4$ is not hydrogen) regioisomeric ring-extended macrocyclic ketones can additionally be obtained, depending on which half of the cyclic system the two carbon atoms of the original vinyl group of the starting material are incorporated according to the method described above. This naturally also applies when $R^4$ represents two or more substituents.

Using the described thermo-isomerization process, it is possible to produce, from tertiary cyclic allyl or propargyl alcohols, macrocyclic ketones which can in turn be converted efficiently and in a simple manner by known methods into cyclic tertiary allyl or propargyl alcohols, which can in turn be used as starting materials in the described thermo-isomerization method. The described process therefore additionally offers, by repetition of the process, the options of producing, by iteration, in each case also the macrocyclic ketones ring-expanded by four, six, eight, etc. carbon atoms, in which case only two synthesis stages are required per repeat cycle.

In the same way, the described method can also be used for the analogous etherified derivatives of the parent macrocyclic tertiary alcohols, for example, trialkyl silyl ethers, in particular for trimethylsilyl ethers (when thus $R^5$ in formula IIa or IIb represents a trimethylsilyl group), where then, in an analogous manner, firstly, however, in each case mixtures of the corresponding ring-expanded cyclic trimethylsilyl enol ethers are obtained. Hydrolysis of these trimethylsilyl enol ether mixtures then likewise leads again to the same ketones which can be obtained from the corresponding parent alcohols in a direct manner, without prior derivatization by a suitable silyl group and thus without the additionally required hydrolysis stage.

By carrying out the thermo-isomerization in the gas phase, the method according to the invention can take place without the use of solvent and thus in a manner which respects environmental protection, if the starting material is vaporized directly into the gas phase and passed to the reactor unit. Expedient design of the apparatus additionally allows the described thermo-isomerization method to be carried out continuously and thus potentially also permits process automation. In the scientific specialist literature there are many descriptions of different apparatus for carrying out very diverse analogous chemical conversion processes in the gas phase using temperatures of up to about 1000° C. (gas-phase flow thermolysis or short-term vacuum pyrolysis apparatuses).

The method according to the invention for producing macrocyclic ketones is based on the thermo-isomerization of tertiary macrocyclic allyl alcohols or propargyl alcohols in the gas phase at temperatures of from 500 to 700° C. To carry out the method according to the invention, the alcohol used as starting material is either initially introduced in a vaporization unit, or is added via a metering device, such as a metering or spray pump, from a storage vessel, preferably either in undiluted form or else in dissolved form in a suitable inert solvent (such as, for example, xylene) in a continuous manner and heated, under reduced pressure depending on the boiling point of the starting material used to temperatures in the range from about 100–300° C., preferably in the range from 120–250° C. and thereby converted into the gas phase. The alcohol preheated in the vaporization unit is then passed into the gas phase, optionally also using a regulatable inert gas stream, where the inert gas can, for example, be nitrogen, argon or helium, and, at reduced pressure, through a suitably dimensioned and appropriately shaped reactor unit which is heated to temperatures between 500 and 700° C., where the macrocyclic tertiary allyl or propargyl alcohol used according to the present description of the thermo-isomerization process according to the invention is converted into the corresponding macrocyclic ketone.

The reactor unit is generally expediently tubular in shape, and is preferably made of an inert material which is thermostable and does not interfere with the course of the isomerization reaction, for example, certain types of high-melting glass. It can be arranged horizontally or vertically or at any desired incline, and it can be heated independently of the vaporization unit in a generally known manner, for example, using an electric heating mantle. The temperature range required for the described thermo-isomerization method depends simultaneously on a number of factors, for example, the prevailing pressure within the reactor, the configuration and dimensions of the reactor vessel, the size of the inert-gas stream (flow) and the rate of addition and rate of vaporization of the starting material or of its solutions, and on the solvent. It is preferably in the range of from 500 to 700° C. Below about 450° C. the thermo-isomerization process is so slow that primarily unchanged starting material and in some instances dehydration products are found, whereas at temperatures above 700° C. decomposition products and undesired secondary reactions are observed to an increasing degree. The preferred temperature range for as complete as possible a conversion of the starting materials used in the described thermo-isomerization method is directly dependent on the stated individual reactor parameters and often is above 550° C., particularly optimally in the range from 570° C.–670° C., particularly when the process is carried out without solvents with a gentle inert gas stream or in a high vacuum without inert gas stream and without a filler packing. Preferably, the described thermo-isomerization process is carried out at reduced pressure, particularly advantageously at a vacuum in the range from about 1 to 10 mbar (1–10 hPa), in any case expediently below the saturated vapor pressure of the alcohol used as starting material, but the desired product formation can be observed in the inert-gas stream also at a less greatly reduced pressure, for example, that obtained by using a water-jet vacuum or a laboratory membrane vacuum pump. The pressure in the apparatus and thus at the same time the contact time in the reactor unit can additionally be influenced by the regulation of the inert-gas stream, or during injection of liquid starting materials, through the rate of addition or in the case of initially solid starting materials, through the rate of vaporization.

In the downstream condenser unit, the gaseous reaction products obtained by the thermo-isomerization method are cooled to room temperature or below by means of a suitable medium by known methods and in so doing liquefied again (or in individual cases resublimed) and then collected in a receiver. An outlet valve on the receiver and a further valve (tap) on the collecting container which can be detached from the receiver permits, in accordance with the Normag-Thiele attempt, the collection and the removal at least of the liquid reaction products also under continuing reduced pressure within the described thermo-isomerization apparatus, in particular in the vaporization, reactor and condenser unit, meaning that a continuous permanent operation of the apparatus can also be ensured. The reduced pressure in the apparatus is generated by a vacuum-pump unit with suitable suction capacity, particularly advantageously by means of a high-vacuum pump. It is possible to connect between vacuum pump and apparatus further cooling traps a suitable cooling medium to receive readily volatile by-product components.

Using the method according to the invention, the following novel compounds have been produced:
2-methylcyclotetradecanone,
3-methylcycloheptadecanone,
5-methylcycloheptadecanone,
3-methylcycloheptadecanone,
4-ethylcyclotetradecanone, 3,4-dimethylcyclotetradecanone.

The tertiary macrocyclic allyl alcohols of the formula IIa required as starting materials for the thermo-isomerization process can be produced readily by known methods, for example preferably by the addition of suitable organometallic-alkenyl compounds, such as magnesium or lithium-1-alkenyls on to the corresponding macrocyclic ketones. By known methods yields of up to 70% of macrocyclic allyl or propargyl alcohols are obtained by the addition of common vinyl Grignard reagents, such as, vinylmagnesium chloride or vinylmagnesium bromide, or e.g. also of corresponding 1- or 2-substituted vinyl-Grignard compounds or metalloalkynide derivatives, as are shown as substituents on C(1) of the tertiary macrocyclic alcohols of the formula IIa, and where $R^1$ to $R^3$ have the meanings given in the description, are, for macrocyclic ketones.

Better yields of macrocyclic allyl alcohols of the formula IIa, mostly in the region around or also above about 90% can be obtained by transferring a precomplexation method to macrocyclic ketones. This can be achieved with catalytic or substoichiometric or stoichiometric amounts of an anhydrous Lewis acid, such as, of cerium trichloride ($CeCl_3$) at temperatures in the range from about 0–40° C., where improved yields of tertiary allyl alcohols were obtained during the subsequent addition of the organometallic-alkenyl used. The addition of from 1.01 to about 2 mol equivalents, preferably from 1.5 to 1.8 mol equivalents of the organometallic-alkenyl solution in absolute THF to the suspension of the macrocyclic ketone precomplexed in the described manner, usually proceeds with noticeable heat of reaction and therefore advantageously is conducted such that the rate of the addition is chosen depending on the existing cooling capacity of the reactor system such that the temperature of the precooled reaction mixture does not exceed 30 to about 40° C. The temperature is then maintained, with stirring, for about a further 10 to 120 minutes at 35 to 40° C., and, after monitoring the course of the reaction, for example by gas chromatography of the reaction mixture, where necessary 0.1 to 0.2 mol equivalents of the alkenyl or alkynyl compound is again added for as complete as possible a conversion of the ketone used. The tertiary macrocyclic allyl or propargyl alcohol obtained following hydrolysis of the reaction mixture is either purified by distillation in a high vacuum or by recrystallization or chromatography, or else used in the form of the crude product directly for subsequent thermo-isomerization as starting material.

Using the above-described method it was possible to produce the following novel tertiary macrocyclic allyl alcohols of the formula IIa or propargyl alcohols of the formula IIb required for the thermo-isomerization process as starting material:

1-vinyl-1-cycloundecanol
1-vinyl-1-cyclotridecanol
1-vinyl-1-cyclotetradecanol
1-vinyl-1-cyclopentadecanol
(syn/anti)-2-methyl-1-vinyl-1-cyclododecanol
(syn/anti)-3-methyl-1-vinyl-1-cyclopentadecanol
(E/Z)-1-(1-propen-1-yl)cyclododecanol
(E/Z)-1-(1-propenyl)cyclotridecanol
(E/Z)-1-(1-propenyl)cyclotetradecanol
(E/Z)-1-(1-propen-1-yl)cyclopentadecanol
1-(1-methylethenyl)cycloundecanol
1-(2-methyl-1-propenyl)cyclododecanol
(E/Z)-1-(2-buten-2-yl)cyclododecanol
1-ethynylcyclotridecanol
1-(1-propynyl)dodecanol
(E/Z)-1-(trimethylsilyloxy)-1-(1-propenyl) cyclododecanol).

EXAMPLES

I. Alkenyl and 1-alkynyl Grignard Reactions a) Drying of cerium trichloride:

100 g of cerium(III) chloride heptahydrate (Fluka) (0.268 mol) was dried with continuous rotation in a Büchi Kugelrohr oven in a high vacuum by firstly heating for 5–6 h at an air bath temperature of 70–80° C., then for 3–4 h at 110–120° C. and finally overnight (about 12 h) at 150–160° C. The eliminated water was collected in cool traps (liquid nitrogen cooling), these were changed a number of times until finally no more condensation was observed. After thawing, the liquid content of the cool traps was collected and thus finally about 34 ml of water and 65 g of dried pulverulent cerium(III) chloride were obtained. This was transferred to a storage vessel under an inert gas atmosphere and stored under an argon atmosphere. Even after storage for several months at room temperature, no loss in activity for the Grignard reactions described below was found.

b) Precomplexation of the ketone (typical, generalizable procedure):

36.4 g of cyclododecanone (0.2 mol) was suspended together with 5 g of anhydrous $CeCl_3$ (0.02 mol, 0.1 mol equiv.) at room temperature in 100 ml of absolute THF and vigorous stirred under an inert-gas atmosphere for 1 to 2 hours until a whitish to intensively yellow homogeneous suspension of partially gel-like consistency was obtained.

1. Vinyl Grignard reaction (typical, generalizable procedure):

1.1 1-Vinyl-1-cyclododecanol from cyclododecanone:

To the suspension of the ketone activated by precomplexation with $CeCl_3$ was added 320 ml of a 1-molar solution of vinylmagnesium bromide in abs. THF (corresponding to about 0.32 mol of vinylmagnesium bromide, about 1.6 mol equiv.) within about 5 min with stirring such that, with temporary use of a cooling bath (ice bath), the temperature inside the reaction vessel did not exceed the temperature range from 35–40° C. After the exothermic reaction had subsided, the now grayish-green reaction mixture was stirred for about a further 30 min at 35–40° C., and the course of the reaction was monitored by gas chromatographic analysis. Depending on the activity of the cerium (III) chloride used, this usually reveals a starting material conversion significantly above 70% already just after 15 minutes, where then, if need be, still incompletely reacted ketone can be reacted by the addition of further about 0.1 to 0.2 mol equivalents of vinylmagnesium bromide (above 80% conversion).

Work-up: The reaction mixture was left to cool to room temperature and was poured it on to 1 l of iced water, adding a layer of the extractant (toluene or TBME) and slowly admixed, with stirring, with an approximately 5–10% strength aqueous hydrochloric acid solution until the slime- or gel-like consistency of the mixture had disappeared (about pH 3 or below) and, with the appearance of a yellow to brownish coloration, a clear phase boundary could finally be recognized. The aqueous phase was removed and the organic phase was washed a number of times, firstly with water, then with sodium hydrogencarbonate solution or with about 5% strength NaOH solution, then again with water, conc. aqueous NaCl solution and finally dried over sodium sulfate or magnesium sulfate. After the extractant had been evaporated under reduced pressure, the crude product obtained was 41.3 g of 1-vinyl-1-cyclododecanol (crude yield 97% of theory, GC purity>86%, comprises about 12–14% cyclododecanone) was obtained as a slightly yellowish solid. This was either used directly for the subsequent thermo-isomerization or purified beforehand either by Kugelrohr distillation at a high vacuum and recrystallization from hexane/TBME (95:5, v:v) or by chromatography over silica gel (hexane:TBME 9:1): colorless, wax-like solid with melting point 53° C.

$^1$H-NMR (300 MHz, $CDCl_3$): 5.98 (dd, J=10.8, 17.4 Hz, 1 H), 5.20 (dd, J=1.4, 17.4 Hz, 1 H), 5.01 (dd, J=1.4, 10.8 Hz, 1 H), 1.9–1.2 (m, 23 H). $^{13}$C-NMR (75 MHz, $CDCl_3$): 145.3 (d); 111.0 (t); 75.3 (s); 34.6 (2), 26.3 (2), 25.9, 22.5 (2), 22.1 (2), 19.5 (2) (6 t).EI-MS (GC/MS): 210.2 (2, $M^{+\circ}$), 192.2 (50, M-18), 77.7 (98), 67 (100), 55 (97).

In an analogous manner, the following tertiary macrocyclic allyl alcohols were also prepared, by way of example, from the corresponding ketones by the addition of vinylmagnesium bromide:

1.2. 1-Vinyl-1-cyclooctanol from cyclooctanone:
Yield 94%, GC purity>90%
$^1$H-NMR (300 MHz, $CDCl_3$): 6.01 (dd, J=10.8, 17.4 Hz, 1 H); 5.23 (dd, J=1.3, 17.4 Hz, 1 H); 5.13 (dd, J=1.3, 10.8 Hz, 1 H); 1.92–1.25 (m, 15 H). $^{13}$C-NMR (75 MHz, $CDCl_3$): 145.8 (d); 111.1 (t); 75.1 (s); 36.2 (2), 28.1 (2), 24.6, 21.9 (2) (4 t).EI-MS (GC/MS): 154 (2, $M^{+\circ}$), 136 (100, M—$H_2O$).

1.3. 1-Vinyl-1-cyclodecanol from cyclodecanone:
$^1$H-NMR (300 MHz, $CDCl_3$): 5.99 (dd, J=10.8, 17.4 Hz, 1 H); 5.21 (dd, J=1.4, 17.4 Hz, 1 H); 5.01 (dd, J=1.4, 10.8 Hz, 1 H); 1.85–1.25 (m, 19 H). $^{13}$C-NMR (75 MHz, $CDCl_3$): 145.5 (d); 110.9 (t); 76.2 (s); 34.2 (2), 26.7, 26.1 (2), 23.5 (2), 21.1 (2) (4 t).EI-MS (GC/MS): 182 (1, $M^{+\circ}$), 164 (42, M—$H_2O$), 149 (31), 135 (42), 79 (95), 68 (100), 55 (68).

1.4. 1-Vinyl-1-cycloundecanol from cycloundecanone:
Yield 84%.
$^1$H-NMR (300 MHz, $CDCl_3$): 5.98 (dd, J=10.8, 17.4 Hz, 1 H); 5.20 (dd, J=1.4, 17.4 Hz, 1 H); 5.01 (dd, J=1.3, 10.8 Hz, 1 H); 1.76–1.20 (m, 21 H). $^{13}$C-NMR (75 MHz, $CDCl_3$): 145.4 (d); 111.1 (t); 75.8 (s); 36.2, 27.0, 25.9, 25.4, 21.1 (5 t, je 2 $CH_2$). EI-MS (GC/MS): 196.1 (1, $M^{+\circ}$), 178 (15, M—$H_2O$), 169 (18), 149 (17), 135 (20), 111 (55), 97 (80), 83 (100), 70 (95), 55 (100).

1.5. 1-Vinyl-1-cyclotridecanol from cyclotridecanone:
Yield 84%, content according to GC 92%.
$^1$H-NMR (300 MHz, $CDCl_3$): 5.98 (dd, J=10.8, 17.4 Hz, 1 H); 5.21 (dd, J=1.4, 17.4 Hz, 1 H); 5.01 (dd, J=1.4, 10.8 Hz, 1 H); 1.65–1.2 (m, 25 H). $^{13}$C-NMR (75 MHz, $CDCl_3$): 145.4 (d); 111.1 (t); 75.1 (s); 37.4, 27.8, 26.6, 25.4, 25.3, 20.9 (5 t). EI-MS (GC/MS): 224 (1, $M^{+\circ}$), 206 (100, M—$H_2O$).

1.6. 1-Vinyl-1-cyclotetradecanol from cyclotetradecanone:
Yield 98%.
$^1$H-NMR (300 MHz, $CDCl_3$): 5.99 (dd, J=10.8, 17.4 Hz, 1 H); 5.22 (dd, J=1.4, 17.4 Hz, 1 H); 5.03 (dd, J=1.4, 10.8 Hz, 1 H); 1.6–1.2 (m, 27 H). $^{13}$C-NMR (75 MHz, $CDCl_3$): 145.4 (d); 111.3 (t); 75.0 (s); 37.2 (2), 26.43 (2), 26.38, 25.9, 24.0, 23.5, 20.3 (7 t). EI-MS (GC/MS): 224 (1, $M^{+\circ}$), 206 (100, M—$H_2O$).

1.7. 1-Vinyl-1-cyclopentadecanol from cyclopentadecanone:
Yield 92%.
$^1$H-NMR (300 MHz, $CDCl_3$): 5.97 (dd, J=10.8, 17.4 Hz, 1 H); 5.22 (dd, J=1.4, 17.4 Hz, 1 H); 5.03 (dd, J=1.4, 10.8 Hz, 1 H); 1.6–1.2 (m, 29 H). $^{13}$C-NMR (75 MHz, $CDCl_3$): 145.4 (d); 111.3 (t); 75.0 (s); 37.2 (2), 26.43 (2), 26.38, 25.9, 24.0, 23.5, 20.3 (7 t). EI-MS (GC/MS): 252.1 (1, $M^{+\circ}$), 234 (10, M—$H_2O$).

1.8. (syn/anti)-2-Methyl-1-vinyl-1-cyclododecanol from (RIS)-2-methylcyclodecanone:
Yield 98%.
$^1$H-NMR (300 MHz, $CDCl_3$): 5.93/5.88 (dd, J=10.8, 17.3 Hz, 1 H); 5.24/5.23 (dd, J=1.6, 17.3 Hz, 1 H); 5.08/5.06 (dd, J=1.6, 10.8 Hz, 1 H); 2.1–1.1 (m, 22 H), 0.85/0.81 (d, J=6.6 Hz, 3 H). $^{13}$C-NMR (75 MHz, $CDCl_3$): 144.7/142.4 (d); 112.2/111.0 (t); 78.0/77.9 (s); 38.4/35.9 (t); 35.5/34.4 (d); 28.7, 26.8, 26.5, 26.3 (2), 25.0, 24.8, 23.4, 23.1, 23.0, 22.9, 22.8 (2), 22.7, 22.2, 22.1, 20.4, 18.4 (18 t); 14.6/13.6 (q). EI-MS (GC/MS): 224.1 (7, $M^{+\circ}$), 209(9, M-15), 206 (6, M-18).

1.9. (syn/anti)-3-Methyl-1-vinyl-1-cyclopentadecanol from rac. 3-methylcyclopentadecanone:
Yield 93%
$^1$H-NMR (300 MHz, $CDCl_3$) of A: 5.93 (dd, J=10.7, 17.3 Hz, 1 H); 5.18 (dd, J=1.3, 17.3 Hz, 1 H); 5.0 (dd, J=1.3, 10.7 Hz, 1 H); 1.8–1.0 (m, 28 H), 0.99 (d, J=6.6 Hz, 3 H); of B: 5.97 (dd, J=10.8, 17.4 Hz, 1 H); 5.21 (dd, J=1.4, 17.4 Hz, 1 H); 5.0 (dd, J=1.4, 10.8 Hz, 1 H); 1.8–1.0 (m, 28 H), 0.88 (d, J=6.5 Hz, 3 H). $^{13}$C-NMR (75 MHz, $CDCl_3$) of A (main isomer): 146.0 (d); 110.9 (t); 75.7 (s); 46.0, 38.9, 37.2 (3 t), 27.0 (d) 22.2 (q), 26.6 (t); of B: 146.0 (d); 110.9 (t); 75.7 (s); 46.0, 38.9, 37.2 (3 t), 27.0 (d) 22.2 (q), 26.6 (t); of A or B: 27.4, 27.2, 27.1, 27.0, 26.9, 26.7, 26.6, 26.4, 26.3, 26.2, 26.0, 25.9 (2), 25.8, 25.0, 24.9 (16 t); of A: 22.2 (q), 22.6 (t); of B: 21.7 (q), 21.2 (t).

EI-MS (GC/MS) of A: 266 (2, M$^{+\circ}$), 248 (28, M—H$_2$O), 233 (7), 219 (11), 121 (40),107 (55), 94 (58), 67 (83), 55 (100); of B: 266 (4, M$^{+\circ}$), 248 (100, M—H$_2$O), 233 (12), 219 (16), 121 (30), 107 (42), 67 (55), 55 (100).

1.10. (syn/anti)-2-Ethyl-1-vinyl-1-cyclododecanol from (R/S)-2-ethylcyclodecanone:

Yield 98%.

$^1$H-NMR (300 MHz, CDCl$_3$) of the diastereoisomer mixture: 5.93/5.88 (dd, J=10.8, 17.3 Hz, 1 H); 5.24/5.23 (dd, J=1.6, 17.3 Hz, 1 H); 5.08/5.06 (dd, J=1.6, 10.8 Hz, 1 H); 2.1–1.1 (m, 24 H), 0.97/0.91 (2t, J=7.3 Hz, 3 H). $^{13}$C-NMR (75 MHz, CDCl$_3$): 144.7/143.0 (d); 111.7/110.7 (t); 78.7/78.6 (s); 43.0/41.4 (d); 39.2, 37.0, 28.2, 26.7, 26.6, 25.9, 25.7 (2), 24.8, 23.8, 23.7, 23.6, 23.5, 23.4, 23.2, 23.1, 23.0, 22.8, 22.4, 22.2, 20.6, 18.6 (22 t); 14.7/13.2 (q).

2. Grignard reactions with alkyl-substituted vinyl halides:

a) 1-Propenyl-Grignard reactions 2.1. (E/Z)-1-(1-Propen-1-yl)cyclododecanol:

The solution of the Grignard reagent prepared beforehand from 3.9 g of magnesium (0.16 mol) and 20.6 g of 1-bromo-1-propene (E/Z mixture, 0.17 mol) in 160 ml of absolute THF by customary methods were added, with stirring and via cannulae, to 18.2 g of cyclododecanone (0.1 mol) which had been precomplexed beforehand analogously to Example Ib of the above description with 2.5 g of CeCl$_3$ (10 mmol, 0.1 mol equiv.), the procedure corresponding to that described in Example 1.1. Crude yields of (E/Z)-1-(1-propenylcyclododecanol): 21 g (94%), wax-like solid, GC purity 92% (comprises about 6% cyclododecanone). Purification by recrystallization from hexane:ether 95:5 (v:v). Separation of the E- and Z-isomer by column chromatography (silica gel, hexane, ether, 9:1), whereas the less polar Z-isomer (white solid) eluted first:

Z-Isomer: $^1$H-NMR (300 MHz, CDCl$_3$): 5.50–5.36 (m, 2 H; analysis at 600 MHz reveals 5.46 (dq, J=11.8 Hz, 7.0 Hz), 5.39 dq (J=11.8 Hz, 1.6 Hz)), 1.87 (dd, J=7 Hz, 1.6 Hz, 3 H), 1.75–1.55 (m, 4 H), 1.49–1.2 (m, 19 H). $^{13}$C-NMR (75 MHz, CDCl$_3$): 136.4 (d); 125.8 (d); 76.1 (s); 35.8 (2); 26.5 (2), 26.1 (2), 22.6 (2), 22.3 (2), 19.7 (2) (6 t); 14.5 (q).

E-Isomer (colorless, wax-type solid): $^1$H-NMR (300 MHz, CDCl$_3$): 5.68–5.55 (m, 2H; analysis at 600 MHz reveals 5.64 (dq, J=15.6, 6 Hz), 5.59 (dq, J=15.6, 1.1 Hz)), 1.69 (dd, J=6, 1 Hz, 3 H), 1.68–1.22 (m, 23 H). $^{13}$C-NMR (75 MHz, CDCl$_3$): 138.4 (d); 122.2 (d); 74.9 (s); 35.0 (2); 26.5 (2), 25.9, 22.6 (2), 22.2 (2), 19.6 (2) (6 t); 17.7 (q).

In an analogous manner, the following tertiary macrocyclic allyl alcohols were produced, also by way of example, from the corresponding ketone by the addition of (E/Z)-1-(1-propenyl)magnesium bromide:

2.2. (E/Z)-1-(1-Propenyl)cyclotridecanol from cyclotridecanone:

Yield 82%.

Z-Isomer (white solid) : $^1$H-NMR (300 MHz, CDCl$_3$): 5.50–5.39 (m, 2 H), 1.87 (dd, J=6.5, 1.8 Hz, 3 H), 1.70–1.60 (m, 4 H), 1.35 (br. s-type m, 21 H). $^{13}$C-NMR (75 MHz, CDCl$_3$): 136.5 (d); 125.7 (d); 76.0 (s); 38.8 (2); 27.8 (2), 26.6 (2), 25.4 (4), 21.1 (6 t); 14.3 (q).

E-Isomer (colorless, viscous oil, main isomer): $^1$H-NMR (300 MHz, CDCl$_3$): 5.65–5.55 (m, 2H), 1.69 (d, J=5, 3 H), 1.68–1.46 (m, 4 H), 1.35 (br. s-type m, 21 H). $^{13}$C-NMR (75 MHz, CDCl$_3$): 138.2 (d); 122.2 (d); 74.6 (s); 37.8 (2); 27.9 (2), 26.7 (2), 25.5 (2) 25.4 (2), 21.0 (2), (6 t); 17.7 (q).

2.3. (E/Z)-1-(1-Propen-1-yl)cyclotetradecanol from cyclotetradecanone:

Yield 93%.

Z-Isomer (white solid): $^1$H-NMR (300 MHz, CDCl$_3$): 5.52–5.39 (m, 2 H; analysis at 600 MHz reveals 5.46 (dq, J=12, 6.7 Hz), 5.43 dq (J=12, 1.3 Hz)), 1.87 (dd, J=5.6 Hz, 1.9 Hz, 3 H), 1.68–1.51 (m, 4 H), 1.39–1.18 (m, 21 H). $^{13}$C-NMR (75 MHz, CDCl$_3$): 136.6 (d); 125.7 (d); 75.9 (s); 38.8 (2); 27.8 (2), 26.5 (2), 26.4, 26.0 (2), 23.5 (2), 20.4 (2) (7 t); 14.3 (q).

E-Isomer (main isomer, colorless, viscous oil, which gradually solidifies upon standing to give a solid): $^1$H-NMR (300 MHz, CDCl$_3$): 5.71–5.56 (m, 2H; analysis at 600 MHz reveals 5.65 (dq, J=16 Hz, 6 Hz), 5.59 dq (J=16 Hz, 1.1 Hz)), 1.70 (d, J=5 Hz, 3 H), 1.63–1.18 (m, 27 H). $^{13}$C-NMR (75 MHz, CDCl$_3$): 138.5 (d); 122.4 (d); 74.6 (s); 37.5 (2); 26.5 (2), 26.4, 26.0 (2), 24.0 (2) 23.5 (2), 20.4 (2), (7 t); 17.7 (q).

2.4. (E/Z)-1-(1-Propen-1-yl)cyclopentadecanol from cyclopentadecanone:

Yield 90%.

E/Z-Isomer mixture: $^1$H-NMR (300 MHz, CDCl$_3$): 5.68–5.44 (m)/5.50–5.39 (m, 2 H); 1.87 (d, J=5.8 Hz)/1.69 (d, J=5.2 Hz, 3 H), 1.67–1.20 (m, 29 H). $^{13}$C-NMR (75 MHz, CDCl$_3$): 138.4/136.5 (d); 125.8/122.5 (d); 75.9/74.6 (s); 39.5/38.8; 26.9, 26.6 (3), 26.24, 26.20, 21.9, 21.8; 17.7/14.3 (q).

b) 2-Propenyl-Grignard reactions (typical, analogous procedure):

2.5. 1-(1-Methylethenyl)cyclododecanol from cyclododecanone 14.5 g of cyclododecanone (80 mmol), precomplexation with 1 g of CeCl$_3$ (4 mmol=0.05 mol equiv.); about 100 mmol of 1-propen-2-ylmagnesium bromide (freshly prepared from 2.43 g of magnesium and 14 g of 2-bromo-1-propene in THF). After 2 h, about 15% starting material according to GC. Following customary work-up and Kugelrohr distillation in a high vacuum, 16.8 g (93%) of colorless, viscous oil was obtained, which gradually solidified from standing (comprises 15% cyclododecanone according to GC). Recrystallization twice from hexane at −15° C. gave 12.9 g (72%) of a white crystalline solid.

$^1$H-NMR (300 MHz, CDCl$_3$): 4.84–4.82 (m, 2 H); 1.79 (d, 0.6 Hz, 3H), 1.63 (m$_c$, 4 H); 1.4–1.2 (m, 19 H). $^{13}$C-NMR (75 MHz, CDCl$_3$): 150.6 (s); 110.4 (t); 76.8 (s); 32.8 (2), 26.5 (2), 26.1, 22.5 (2), 22.2 (2), 19.9 (2) (6 t); 18.8 (q).

EI-MS (GC/MS): 224.1 (4, M$^{+\circ}$), 206.1 (28, M—H$_2$O), 55.0 (100).

2.6. 1-(1-Methylethenyl)cycloundecanol from cycloundecanone:

Yield 88%.

$^1$H-NMR (300 MHz, CDCl$_3$): 4.83 (d, J=16.4 Hz, 2 H); 1.78 (d, 0.6 Hz, 3 H), 1.74–1.70 (m, 4 H); 1.64–1.2 (m, 17 H). $^{13}$C-NMR (75 MHz, CDCl$_3$): 150.6 (s); 110.1 (t); 77.3 (s); 34.1 (2), 27.1 (2), 26.1(2), 25.4 (2), 21.5 (2), (5 t); 18.8 (q).

EI-MS (GC/MS): 210.1 (1, M$^{+\circ}$), 192.0 (95, M—H$_2$O), 148.8 (100).

c) Grignard reactions with alkyl-disubstituted vinyl halides:

2.7. 1-(2-Methyl-1-propenyl)cyclododecanol from cyclododecanone:

3.0 g of cyclododecanon (16.5 mmol), precomplexation with 1 g of CeCl$_3$ (4 mmol=0.25 mol equiv.); about 25 mmol of 2-methyl-1-propen-1-ylmagnesium bromide (freshly prepared from 0.6 g of magnesium and 3.5 g of 1-bromo-2-methyl-1-propene (isocrotyl bromide) in THF). After 2 h, about 3% of starting material according to GC. Customary work-up and Kugelrohr distillation in a high vacuum gave 2.9 g (74%) of colorless, viscous oil, which gradually solidified on standing to become wax-like.

$^1$H-NMR (300 MHz, CDCl$_3$): 5.22 (br. s-type m, 1 H); 1.87 (d, J=1.2 Hz, 3 H), 1.69 (d, J=1.2 Hz 3 H); 1.63–1.5 (m, 4 H); 1.48–1.2 (m, 19 H). $^{13}$C-NMR (75 MHz, CDCl$_3$):

134.2 (s); 130.7 (d); 75.1 (s); 36.0 (2) (t), 27.2 (q); 26.4 (2), 25.9, 22.5 (2), 22.2 (2), 19.6 (2) (5 t); 18.9 (q).

EI-MS (GC/MS): 238.1 (8, $M^{+\circ}$), 220.1 (45, M—$H_2O$), 96.0 (100).

2.8. (E/Z)-1-(2-Buten-2-yl)cyclododecanol from cyclododecanone:

9.1 g of cyclododecanone (50 mmol), precomplexation with 2 g of $CeCl_3$ (8 mmol=0.16 mol equiv.); about 80 mmol of (E/Z)-2-buten-2-ylmagnesium bromide (freshly prepared from 2.0 g of magnesium and 10.8 g of 1-bromo-2-methyl-1-propene in THF). After 2 h, about 30% starting material as well as 2 main products (31 and 15%, respectively) according to GC. Customary work-up gave 11.3 g (95%) of a slightly yellowish wax-like solid. Recrystallization twice from hexane at −20° C. gives 4.3 g (36%) of colorless crystals of an E/Z-isomer mixture (about 4:1).

Separation of the isomers by column chromatography over silica gel (hexane/TBME 94:6):

$^1$H-NMR (300 MHz, $CDCl_3$) Isomer A (eluted first, colorless crystals): 5.37 (dq, J=7.3, 1.3 Hz, 1 H), 1.84 (dd, J=7.3, 1.3 Hz, 3 H), 1.72–1.70 (m, 7 H), 1.45–1.25 (m, 19 H). $^{13}$C-NMR (75 MHz, $CDCl_3$): 140.9 (s), 122.8 (d), 77.8 (s), 34.6 (2), 26.4 (2), 26.0 (3 t), 23.2 (q), 22.4 (2), 22.1 (2), 19.6 (3 t), 15.1 (q).

$^1$H-NMR (300 MHz, $CDCl_3$) Isomer B (eluted later, colorless crystals): 5.43 ($m_c$, 1 H), 1.67 (m, 3 H), 1.62–1.55 (m, 7 H), 1.45–1.1 (m, 19 H). $^{13}$C-NMR (75 MHz, $CDCl_3$): 140.8 (s), 118.2 (d), 77.1 (s), 32.7 (2), 26.3 (2), 26.0, 22.4 (2), 22.1 (2) (6 t), 13.3 (q), 11.6 (q).

2.9. (E/Z)-2-Methyl-1-(1-propen-1-yl)cyclododecanol from 2-methylcyclododecanone:

Isomer mixture: characteristic signals in $^{13}$C-NMR (75 MHz, $CDCl_3$): 137.4, 135.4, 135.1, 133.2, 125.7, 124.8, 122.8, 121.4 (8 d); 79.6, 79.2, 77.3, 77.2 (4 s); 37.1, 36.2, 35.6, 34.8 (4 d); 14.5, 14.4, 13.9, 13.5 (4 q). EI-MS (GC/MS): 238.1 ($M^{+\circ}$).

3. Addition of cyclic alken-1-yl derivatives 3.1. 1-(1-cyclohexenyl)cyclododecan-1-ol.

Preparation with 1-chloro-1-cyclohexene according to the literature (cf. Marson et al. *J. Org. Chem.* 1993, 58, 5944–5951, spec. p. 5948; and Adam, *Synthesis* 1994, 176–180).

$^1$H-NMR (300 MHz, $CDCl_3$): 5.62–5.59 (m, 1 H), 2.11–2.01 (m, 4 H), 1.66–1.52(m, 8 H), 1.37–1.22 (m, 19 H). $^{13}$C-NMR (75 MHz, $CDCl_3$): 142.5 (s), 121.1 (d), 76.8 (s), 32.8 (2), 26.5 (2), 26.2, 25.4, 23.9, 23.2, 22.5 (2), 22.2 (2), 19.9 (2).

4. Addition of alkynyl derivatives 4.1. 1-Ethynylcyclododecanol from cyclododecanone:

5.5 g of cyclododecanone (30 mmol), precomplexation with 1 g of $CeCl_3$ (4 mmol=0.13 mol equiv.); about 60 mmol of ethynylmagnesium bromide (120 ml of a 0.5 M solution in THF). After 2 h, about 2–5% starting material and about 90% of a main product, according to GC. Customary work-up gave 5.3 g (85%) of a slightly yellowish solid. Recrystallization from hexane/TBME (9:1, v:v) at 4° C. gives 4.5 g (72%) of colorless, transparent crystals. Ethynylcyclododecanol (technical-grade, GIVAUDAN) was likewise purified by distillation in high vacuum and crystallization from hexane/TBME 9:1 (GC content>97%).

$^1$H-NMR (300 MHz, $CDCl_3$): 2.44 (s, 1 H), 2.12 (s, 1 H), 1.91–1.80 (m, 2 H), 1.75–1.63 (m, 2 H), 1.60–1.2 (m, 18 H). $^{13}$C-NMR (75 MHz, $CDCl_3$): 88.5 (s), 71.4 (d), 70.8 (s), 35.8 (2), 26.1 (2), 25.9, 22.5 (2), 22.2 (2), 19.6 (2) (6 t).

EI-MS: 208 (1, $M^{+\circ}$), 190 (15), 175 (4), 161 (10), 147 (20), 133 (25), 119 (30), 105 (50), 93 (60), 91 (100), 79 (75), 67 (35), 55 (32).

4.2. 1-Ethynylcyclotridecanol from cyclotridecanone:

$^1$H-NMR (300 MHz, $CDCl_3$): 2.44 (s, 1 H), 1.93 (s, 1 H), 1.83–1.67 (m, 4 H), 1.53–1.34 (m, 20 H). $^{13}$C-NMR (75 MHz, $CDCl_3$): 88.2 (s), 71.3 (d), 70.7 (s), 38.8 (2), 27.2 (2), 26.4 (2), 25.4 (2), 25.3 (2), 21.1 (2) (6 t). EI-MS: 222(1, $M^{+\circ}$), 221 (1, M−1), 207(5), 196 (6), 179 (5), 165 (8) 161 (7), 151 (15) 137 (20), 123 (36), 109 (45), 97 (50), 68 (100) 55 (99).

4.3. 1-(1-Propynyl)cyclododecanol from cyclododecanone:

3.64 g of cyclododecanone (20 mmol), precomplexation with 2 mmol of $CeCl_3$ in 30 ml of THF, 30 mmol of 1-propynylmagnesium bromide (corresponding to 60 ml of an approximately 0.5 M solution in THF), only slight exothermy. Following customary work-up, 3.8 g (85%) of a yellowish oil (GC content>92%, which crystallized on standing. Purification by Kugelrohr distillation: 3.6 g (81%) of colorless oil, which solidified to become crystalline.

$^1$H-NMR (300 MHz, $CDCl_3$): 1.83 (s, 3 H), 1.81–1.48 (m, 5 H), 1.35 (br. s-type m, 18 H). $^{13}$C-NMR (75 MHz, $CDCl_3$): 83.8 (s), 79.1 (s), 70.8 (s), 36.2 (2), 26.0 (2), 25.8, 22.4 (2), 22.2 (2), 19.7 (2) (6 t) 3.3 (q). EI-MS (GC/MS): 224.1 (0.5, M+2), 223.1 (2, M+1), 222.1 (3, $M^{+\circ}$), 204.1 (30, M−18), 189.0 (8), 175 (9), 161 (18), 147 (32), 98 (62), 95 (90), 91 (100), 83 (85), 67 (95), 55 (98).

4.4. 1-(1-Propynyl)cyclotridecanol from cyclotridecanone:

$^1$H-NMR: 1.83 (s, 3 H), 1.78–1.62 (m, 5 H), 1.50–1.26 (br. s-type m, 20 H).

$^{13}$C-NMR (75 MHz, $CDCl_3$): 83.7 (s), 79.1 (s), 70.9 (s), 39.2 (2), 27.3 (2), 26.5(2), 25.4 (2), 25.3 (2), 21.3 (2) (6 t) 3.3 (q). EI-MS (GC/MS): 236 (2, $M^{+\circ}$), 235 (1, M−1), 221 (22), 207 (5), 196 (10), 179 (11), 165 (15), 151 (22), 137 (35), 123 (45), 109 (51), 95 (75), 82.5 (100), 67.8 (62), 56 (98).

II. Thermo-isomerizations

Apparatus and general procedure:

The tertiary cyclic alcohol was in each case initially introduced into a Kugelrohr flask (50 or 100 ml, with two opposite ground-glass necks) together with a small magnetic stirrer. After applying an inert-gas feed (stainless steel capillary fused into standard ground-glass attachments) on the rear ground-glass neck, the flask was attached by the front ground-glass joint to the slightly inclined reactor vessel (quartz glass reactor, internal diameter 25 or 40 mm, length 40 cm, heated with Thermolyne tube furnace, 35 cm). At the opposite end of the reactor vessel there was a cool trap (cooling medium liquid nitrogen or dry ice/acetone), which was connected to a high-vacuum pump unit. Following equilibrium of the reactor temperature to 650–660° C. (measured in the middle of the outside wall of the reactor vessel), evacuation of the entire apparatus and establishment of a pressure of about 1 mbar (1 hPa), the flask with the initial charge of alcohol was heated in an airbath (heating mantle of modified Büchi Kugelrohr oven) and thus the starting material, with stirring, vaporized and distilled through the reactor vessel. In this connection, a precision needle valve was used to establish a gentle stream of inert gas (nitrogen, according to Vögtlin model V100 flowmeter 1–5 l/h) and passed via a capillary through the apparatus. At the reactor outlet, a colorless oil began in each case to condense shortly afterwards. This was collected in a collection vessel below the cool trap, where it partially solidified. After about 15–45 min, the starting material was evaporated, in most cases substantially residue-free. After cooling the apparatus, flushing with inert gas, the condensate was washed out of the cool trap with hexane. All of the yields given are typical average values usually from, in each case, at least three thermo-isomerizations carried out separately.

A. Unsubstituted Monocyclic Systems

1.1 Cyclotetradecanone from 1-vinylcyclododecanol:

5 g (23.8 mmol) of 1-vinylcyclododecanol, quartz reactor 25/400 mm, temperature 660° C.±10, vaporization at 125–135° C. (airbath temperature) in about 30 min. Nitrogen stream about 1–2 l/h, vacuum 4–6 mbar. The oily condensate began to crystallize in the cool trap already. 4.4 g (88% crude yield) of a wax-like solid were obtained which, according to GC and GC/MS analyses, comprises as well as 80–85% of the main component also up to about 5% cyclododecanone and about 5–10% other components which, according to the molecular masses found, are dehydrogenation products. Recrystallization twice from hexane at 0° and −20° C., gave 3.6 g (72%) of cyclotetradecanone (GC purity>98%) as colorless needles with a melting point of 56° C.

$^1$H-NMR (300 MHz, CDCl$_3$): 2.44 (t-type centr. m, 4 H), 1.71–1.32 (m, 4 H), 1.29 (br., s-type m, 18 H). $^{13}$C-NMR (75 MHz, CDCl$_3$): 212.2 (s), 40.9, 26.1, 25.8, 25.35, 25.30, 24.5, 22.9 (7 t, je 2 CH$_2$). EI-MS (GC/MS): 211.2 (28), 210.2 (27, M$^{+\circ}$, 152.1 (18), 125.1 (22), 111.1 (28), 96.1 (47), 71(96), 55 (100).

The following compounds were prepared in an analogous manner:

1.2. Cyclodecanone from 1-vinylcyclooctanol.

Crude yield 87%.

$^1$H-NMR (300 MHz, CDCl$_3$): 2.44 (t-type centr. m, 4 H), 1.71–1.32 (m, 4 H), 1.29 (br., s-type m, 10 H). $^{13}$C-NMR (75 MHz, CDCl$_3$): 212.2 (s), 40.9, 26.1, 25.8, 25.35, 25.30, 24.5, 22.9 (7 t, je 2 CH$_2$). EI-MS (GC/MS): 156.1 (8), 155.1 (58), 154.0 (75, M$^{+\circ}$), 125.0 (65), 110.9 (100).

1.3. Cyclododecanone from 1-vinylcyclodecanol.

0.5 g (2.7 mmol) of 1-vinyl-1-cyclodecanol (cf. I.1.3, comprises also about 8–10% cyclodecanone), quartz reactor 25/400 mm, temperature 670° C.±10, vaporization at 95–100° C. (airbath temperature) in about 10 min. Nitrogen stream about 2–2.5 l/h, vacuum 5–6 mbar. 0.45 g (90% crude yield) of a pure white condensate were obtained which partially crystallized into small fine needles. According to GC and GC/MS analyses, the mixture comprises, as main component, about 70% cyclododecanone, as well as 6–8% cyclodecanone and 2–3% starting material. Chromatographic separation of the mixture over silica gel (hexane/TBME 97:3) gave 0.26 g of cyclododecanone (52% isolated yield), which has identical retention times and spectroscopic properties as the commercially available compound (Fluka).

$^1$H-NMR (300 MHz, CDCl$_3$): 2.46 (m$_c$, 4 H), 1.71 (m$_c$, 4 H), 1.30 (br., s-type m, 14 H). $^{13}$C-NMR (75 MHz, CDCl$_3$): 214.8 (s), 40.4 (2), 24.8 (2), 24.7 (2), 24.3 (2), 22.6 (2), 22.4 (6 t). EI-MS (GC/MS): 183.1 (4), 182.1 (10, M$^{+\circ}$), 139.0 (8), 125.0 (13), 111.0 (25), 98.0 (33), 71(35), 55 (100).

1.4. Cyclotridecanone from 1-vinylcycloundecanol.

$^1$H-NMR (300 MHz, CDCl$_3$): 2.44 (m$_c$, 4 H), 1.67 (m$_c$, 4 H), 1.31–1.2 (br., s-type m, 16 H). $^{13}$C-NMR (300 MHz, CDCl$_3$): 212.7 (s), 41.9 (2), 26.4 (2), 25.7 (2), 25.6 (2), 24.4 (2), 23.2 (6 t), EI-MS (GC/MS): 198.2 (5), 197.1 (33), 196.0 (40, M$^{+\circ}$), 153.0 (15), 149.0 (25), 138 (30) 125.0 (35), 111.0 (35), 98.0 (33), 71(35), 55 (100).

1.5. Cyclopentadecanone from 1-vinylcyclotridecanol.

$^1$H-NMR (300 MHz, CDCl$_3$): 2.41 (t-type m$_c$, 4 H), 1.64 (m$_c$, 4 H), 1.37–1.30 (br., s-type m, 20 H). $^{13}$C-NMR (75 MHz, CDCl$_3$): 212.5 (s), 42.0 (2), 27.5 (2), 26.70 (2), 26.66 (2), 26.4 (2), 26.2 (2), 23.4 (2) (7 t). EI-MS (GC/MS): 226.1 (2), 225.1 (8), 224.1 (13, M$^{+\circ}$), 166.1 (8), 149.0 (8), 135 (10) 125.0 (15), 111.0 (18), 98.0 (21), 71(66), 55.0 (100).

1.6. Cyclohexadecanone from 1-vinylcyclotetradecanol.

$^1$H-NMR (300 MHz, CDCl$_3$): 2.40 (m$_c$, 4 H), 1.64 (m$_c$, 4 H), 1.32–1.25 (br., s-type m, 22 H). $^{13}$C-NMR (75 MHz, CDCl$_3$): 212.2 (s), 41.9, 27.5, 27.1, 26.9, 26.5 (2), 26.4, 23.3 (8 t). EI-MS (GC/MS): 239.2 (10, M+1), 238.1 (43, M$^{+\circ}$), 223.1 (8), 209.1 (5), 163.0 (12), 149 (18), 135 (28), 125.0 (53), 111.0 (45), 98.0 (76), 82.0 (72), 71.0(100), 58.0 (95), 55.0 (99).

1.7. Cycloheptadecanone from 1-vinylcyclopentadecanol.

$^1$H-NMR (300 MHz, CDCl$_3$): 2.39 (m$_c$, 4 H), 1.62 (m$_c$, 4 H), 1.32–1.25 (br., s-type m, 24 H). $^{13}$C-NMR (75 MHz, CDCl$_3$): 212.0 (s), 42.2, 28.1, 27.7, 27.5, 27.2, 27.1, 26.8, 23.6, (16 t). EI-MS (GC/MS): 253.2 (4, M+1), 252.1 (20, M$^{+\circ}$), 237.1 (3), 234.1 (4), 223.1 (4), 210.1 (5), 194.1 (6), 163.0 (7), 152 (8), 149.0 (8), 135 (17), 125.0 (32), 111.0 (25), 98.0 (58), 82.0 (45), 71.0(100), 58.0 (97), 55.0 (99).

B. Monocyclic Systems Substituted on the Ring Perimeter

1.8. 4-Methylcyclotetradecanone and 2-methylcyclotetradecanone from (syn/anti)-2-methyl-1-vinyl-1-cyclododecanol

0.8 g (4.4 mmol) of 2-methyl-1-vinyl-1-cyclododecanol, quartz reactor 25/400 mm, temperature 670° C.±10, vaporization at 120–135° C. (airbath temperature) in about 15 min. Nitrogen stream about 1.5–2 l/h, vacuum 3–5 mbar. 0.7 g (87% crude yield) of a water-clear, substantially colorless condensate was obtained, which, according to GC and GC/MS analysis, comprised, as main component, about 60% 4-methylcyclotetradecanone and 5% 2-methylcyclotetradecanone (m/e in each case 224), as well as 2–8% cyclododecanone and further dehydrogenation and fragmentation products. The same type of products were also obtained with a quartz reactor with a length of 1 m and an internal diameter of 25 mm at 570° C.±10.

$^1$H-NMR (300 MHz, CDCl$_3$) main component A: 2.61–2.24 (m, 4 H), 1.82–0.95 (m, 21 H); 0.88 (d, $^3$J=6.3 Hz, 3 H). $^{13}$C-NMR (75 MHz, CDCl$_3$): 211.9 (s), 40.9, 38.9, 32.2, 29.7 (4 t), 29.5 (d), 25.7, 25.6, 25.5, 25.2, 24.9, 24.5, 23.1 (8 t), 19.9 (q).

In the $^1$H-NMR spectrum of the mixture, the secondary component B (2-methylcyclotetradecanone, ratio about 1:12) can be characterized by a doublet at 1.06 ppm (J=6.7 Hz), and in the $^{13}$C-NMR spectrum by a carbonyl band at 215 ppm, and a doublet at 45.4 ppm and the quartet at 17.0 ppm.

1.9. 3-Methylcycloheptadecanone and 5-methylcycloheptadecanone from (syn/anti)-3-methyl-1-vinyl-1-cyclopentadecanol.

0.5 g (2.1 mmol) of 3-methyl-1-vinyl-1-cyclopentadecanol quartz reactor 25/400 mm, temperature 670° C.±10, vaporization at 145–170° C. (airbath temperature) in about 15 min. Nitrogen stream about 2–2.5 l/h, vacuum 5–8 mbar. About 0.4 g of a water-clear, substantially colorless condensate was obtained which, according to GC and GC/MS analysis, comprised the two main components (about 34% and 28%) 3-methylcycloheptadecanone and 5-methylcycloheptadecanone, both with m/e 266), as well as smaller amounts of dehydrogenation and fragmentation products.

$^1$H-NMR spectrum (300 MHz, CDCl$_3$) of the mixture: 2.51–2.4 (m), 1.7–1.1 (m); 0.92 (d, J=6.7 Hz), 0.86 (d, J=6.3 Hz), integral ratio about 1:1. $^{13}$C-NMR (75 MHz, CDCl$_3$): 211.2, 211.6 (2 s); 31.5 29.0 (2 d); 20.6, 20.1 (2 q).

EI-MS (GC/MS) of component A: 266.1 (25, M$^{+\circ}$), 248.1 (48), 208.1 (12), 149.0 (15), 125.0 (19), 109.0 (45), 97.0 (52), 69.0 (76), 55.0 (100). of component B: 266.1 (30, M$^{+\circ}$), 251.1 (18), 237.1 (38), 223.0 (15), 208.1 (12), 149.0 (10), 125.0 (45), 111.0 (32), 97.0 (53), 85 (72), 69.0 (78), 55.0 (100). (cf. II.2.4)

1.10. 4-Ethylcyclotetradecanone from 2-ethyl-1-vinyl-1-cyclododecanol:

1 g (4.2 mmol) of 2-ethyl-1-vinyl-1-cyclododecanol, quartz reactor 25/1000 mm, temperature 570° C.±10, vaporization at 135–155° C. (airbath temperature) in about 15 min. Nitrogen stream about 1.5–2 l/h, vacuum 3–5 mbar. 0.8 g (80% crude yield) of a water-clear, colorless condensate was obtained which, according to GC and GC/MS analysis, comprised, as main component, more than 60% of 4-ethylcyclotetradecanone and 5% of 2-ethylcyclotetradecanone (m/e in each case 238), as well as further dehydrogenation and fragmentation products.

$^1$H-NMR (300 MHz, CDCl$_3$) 2.65–2.2 (m, 4 H), 1.85–1.10 (m, 23 H); 0.88 (t, $^3$J=7 Hz, 3 H). $^{13}$C-NMR (75 MHz, CDCl$_3$): 212.2 (s); 41.5, 38.3 (2 t); 36.5 (d); 29.4,26.3, 26.1, 25.7 (2), 25.6 (2), 25.0, 24.7, 23.6, 22.6 (11 t), 11.0 (q). EI-MS (GC/MS): 238.1 (M$^{+\circ}$).

2.1. (R/S)-3-Methylcyclotetradecanone (normuscone) from (E/Z)-1-(1-propenyl)cyclododecanol.

2.3 g (10.2 mmol) of (E/Z)-1-(1-propenyl)cyclododecanol quartz reactor 25/400 mm, temperature 660° C.±10, vaporization at 120–135° C. (airbath temperature) in about 15 min. Stream of nitrogen about 0.5–1 l/h, vacuum 3–5 mbar. 2.0 g (87% crude yield) of a water-clear, substantially colorless condensate was obtained which, according to GC and GC/MS analysis, comprised, as main component, about 45–55% 3-methylcyclotetradecanone, as well as 2–8% cyclododecanone and 4–10% starting material and, in smaller amounts, dehydrogenation and fragmentation products. Chromatographic separation of the mixture over silica gel (hexane/TBME 97:3) gave 0.77 g of 3-methylcyclotetradecanone (33% isolated yield) as colorless oil with a typical musk-like odor which gradually crystallizes upon storage in a refrigerator at 4° C.

$^1$H-NMR (300 MHz, CDCl$_3$): 2.45–2.36 (m, 3 H; fine analysis reveals 2.43 (dd, $^2$J=15 Hz, $^3$J=5 Hz, 1 H, H$_a$—C(2)), 2.41 (t, $^3$J=6.7 Hz, 2 H, H$_2$—C(14)); 2.19 (dd, $^2$J=15 Hz, $^3$J=5 Hz, 1 H, H$_b$—C(2); 2.10 (m$_c$, 1 H, H—C(3)), 1.64 (m$_c$, 2 H, H$_2$C(13)), 1.37–1.20 (br. m, 18 H); 0.93 (d, $^3$J=6.7 Hz, 3 H, H$_3$C—C(2)). $^{13}$C-NMR (75 MHz, CDCl$_3$): 212.0 (s), 49.5, 41.0, 33.7 (3 t), 28.8 (d), 26.3, 26.1, 25.6, 25.4, 25.3, 25.1, 24.7, 23.4, 22.3 (9 t), 20.7 (q) MS (GC/MS): 226.2 (2, M+2), 225.1 (13, M+1), 224.1 (50, M$^{+\circ}$), 209.1 (28), 195.1 (30), 181.0 (15), 166.0 (38), 125.0 (52), 111.0 (48), 97.0 (50), 85 (100), 71 (52), 55 (51).

2.2. (R/S)-3-Methylcyclopentadecanone (muscone) from (E/Z)-1-(1-propenyl)cyclotridecanol.

2.4 g (10 mmol) of (E/Z)-1-(1-propenyl)cyclotridecanol, quartz reactor 25/400 mm, temperature 660° C.±10, vaporization at 140–155° C. (airbath temperature) in about 15 min. Nitrogen stream about 1.5–2.5 l/h, vacuum 4–6 mbar. 1.9 g (79% crude yield) of a water-clear, substantially colorless condensate was obtained which, according to GC and GC/MS analyses, comprises, as main component, about 45–55% 3-methylcyclopentadecanone, as well as 2–6% cyclododecanone and 4–10% starting material and, in smaller amounts, dehydrogenation and fragmentation products. Chromatographic separation of the mixture over silica gel (hexane/TBME 97:3) gave 0.68 g of 3-methylcyclopentadecanone (28% isolated yield) as a colorless oil with characteristic musk-like odor which has identical retention times and spectroscopic properties to a reference sample of rac. muscone.

$^1$H-NMR (300 MHz, CDCl$_3$): 2.46–2.38 (m, 3 H; fine analysis reveals 2.43 (d, $^2$J=15 Hz, H$_a$—C(2)), 2.41 (t, $^3$J=6.7 Hz, 2 H, H$_2$—C(15)); 2.17 (dd, $^2$J=15 Hz, $^3$J=5.2 Hz, 1 H, H$_b$—C(2); 2.04 (m$_c$, 1 H, H—C(3)), 1.64 (m$_c$, 2 H, H$_2$C(14)), 1.36–1.22 (br., s-type m, 20 H); 0.94 (d, $^3$J=6.7 Hz, 3 H, H$_3$C—C(2)). $^{13}$C-NMR (75 MHz, CDCl$_3$): 212.0 (s), 50.4, 42.1, 35.6 (3 t), 29.0 (d), 27.6, 27.1, 26.8, 26.7, 26.6, 26.5, 26.3, 26.2, 25.1, 23.0 (10 t), 21.0 (q).MS (GC/MS): 240.2 (3), 239.1 (9), 238.1 (21, M$^{+\circ}$), 223.1 (12), 209.1 (18), 195.1 (5), 180.1 (8), 125.0 (25), 111.0 (18), 97.0 (35), 85 (45), 69 (48), 55 (100).

2.3 (R/S)-3-Methylcyclohexadecanone from (E/Z)-1-(1-propenyl)cyclotetradecanol.

Isolated yield 29%.

$^1$H-NMR (300 MHz, CDCl$_3$): 2.44–2.36 (m, 3 H); 2.17 (dd, $^2$J=15 Hz, $^3$J=5.2 Hz, 1 H), 2.07 (m$_c$, 1 H), 1.58 (m$_c$, 2 H), 1.30–1.22 (m, 22 H); 0.93 (d, $^3$J=6.7 Hz, 3 H). $^{13}$C-NMR (75 MHz, CDCl$_3$): 211.5 (s), 50.1, 42.0, 35.4 (3 t), 29.0 (d), 27.4 (2), 26.9, 26.8, 26.5, 26.4, 26.3, 26.2 (2), 25.3, 22.8 (11 t), 20.6 (q).MS (GC/MS): 253.1 (33, M+1), 252.1 (52, M$^{+\circ}$), 223.1 (60), 194.0 (30), 149 (35) 135 (52), 125.0 (88), 111.0 (88), 97.0 (30), 69.0 (95), 55.0 (100).

2.4 (R/S)-3-Methylcycloheptadecanone from (E/Z)-1-(1-propenyl)cyclopentadecanol.

Isolated yield 27%.

$^1$H-NMR (300 MHz, CDCl$_3$): 2.43–2.35 (m, 3 H); 2.17 (dd, $^2$J=15 Hz, $^3$J=5.2 Hz, 1 H), 2.04 (m$_c$, 1 H), 1.58 (m$_c$, 2 H), 1.30–1.22 (m, 24 H); 0.94 (d, $^3$J=6.7 Hz, 3 H). $^{13}$C-NMR (75 MHz, CDCl$_3$): 211.5 (s), 50.3, 42.4, 35.8 (3 t), 29.0 (d), 28.0 (2), 27.6, 27.5, 27.3, 27.1, 26.9, 26.8 (2), 26.7, 25.7, 23.3 (12 t), 20.6 (q). MS (GC/MS): 267.2 (5, M+1), 266.1 (24, M$^{+\circ}$), 237.1 (12), 136 (13), 125.0 (18), 111.0 (18), 97.0 (30), 85.0 (45), 81.0 (42), 69.0 (53), 55.0 (100).

2.5. (R/S)-2-Methylcyclotetradecanone from 1-(1-methylethenyl)cyclododecanol.

Isolated yield 70%.

$^1$H-NMR (300 MHz, CDCl$_3$): 2.70–2.34 (m, 3 H), 1.81–1.15 (m, 22 H), 1.05 (d, J=7 Hz, 3 H). $^{13}$C-NMR (75 MHz, CDCl$_3$): 215.3 (s), 45.6 (d), 38.4, 33.0, 26.4 (2), 26.1, 25.7, 25.4, 24.9, 24.8, 24.7, 24.6, 21.8 (12 t), 17.2 (q). EI-MS (GC/MS): 226.2 (5, M+2), 225.1 (35, M+1), 224.1 (60, M$^{+\circ}$), 195.1 (18), 139.0 (30), 111.0 (43), 98.0 (50), 85 (68), 70 (90), 55 (100).

2.6. (R/S)-2-Methylcyclotridecanone from 1-(1-methylethenyl)-cycloundecanol.

Isolated yield 60%.

$^1$H-NMR (300 MHz, CDCl$_3$): 2.70–2.56 (m, 2 H), 2.39–2.29 (m, 1 H), 1.86–1.10 (m, 20 H), 1.04 (d, J=6.9 Hz, 3 H). $^{13}$C-NMR (75 MHz, CDCl$_3$): 215.4 (s), 46.3 (d), 40.3, 33.0, 26.6, 26.3, 26.2, 25.6, 25.0, 24.7, 24.4, 24.3, 22.7 (11 t), 17.0 (q). EI-MS (GC/MS): 212.2 (5, M+2), 211.1 (33, M+1), 210.1 (45, M$^{+\circ}$), 181 (33), 153 (35), 139 (32), 111 (34), 97 (35), 72 (38), 55 (100).

2.7. 3,3-Dimethylcyclotetradecanone from 1-(2-methyl-1-propenyl)cyclododecanol $^1$H-NMR (300 MHz, CDCl$_3$): 2.42–2.38 (t-type m, 2 H), 2.34 (s, 2 H), 1.64–1.59 (m, 16 H), 1.55–1.23 (m, 2 H), 1.14–1.09 (m, 2 H), 1.00 (s, 6 H). $^{13}$C-NMR (75 MHz, CDCl$_3$): 210.4 (s), 51.0, 42.3 (2 t), 41.0 (s), 38.8, 33.3 (2 t), 29.5 (2) (q), 27.0, 26.2 (2), 25.6, 25.1, 24.1, 22.6, 22.1 (8 t). EI-MS (GC/MS): 239.1 (3), 238.0 (8, M$^{+\circ}$), 223.1 (5), 125.0 (18), 111.0 (22), 97.0 (22), 83 (35), 69 (59), 55 (100).

2-Methyl-2-pentadecen-4-one was identified as second component (29%).

2.8. (cis/trans)-2,3-Dimethylcyclotetradecanone from 1-(2-buten-2-yl)cyclododecanol.

$^1$H-NMR (300 MHz, CDCl$_3$): 2.86–2.7 (m, 1 H), 2.64–2.48 (m, 2 H), 2.27–1.1 (m, 21 H), 1.01 (d, J=6.9 Hz, 3 H), 0.95 (d, J=6.9 Hz, 3 H). $^{13}$C-NMR (75 MHz, CDCl$_3$): 213.0 (s), 51.0 (d), 38.1 (t), 34.3 (d), 29.3, 27.9, 26.2, 25.8, 24.9, 24.8, 24.4, 24.3, 24.1, 20.4 (10 t), 17.4, (q) 8.8

(q).EI-MS(GC/MS): 238.1 (35, M$^{+\circ}$), 223.1 (38), 209.1 (80), 191.1 (34), 181.0 (38), 166 (25), 139.0 (100) 125 (80), 111 (85), 98 (88), 83 (95), 69 (92), 55 (98).

2.9. 3,4-Dimethylcyclotetradecanone from (E/Z)-2-methyl-1-(1-propen-1-yl)cyclododecanol:

1 g (4.2 mmol) of (E/Z)-2-methyl-1-(1-propen-1-yl) cyclododecanol (cf. I.2.9) comprises about 2–4% 2-methylcyclododecanone), quartz reactor 25/1000 mm, temperature 570° C.±10, vaporization at 135–155° C. (airbath temperature) in about 15 min. Nitrogen stream about 1.5–2 l/h, vacuum 3–5 mbar. 0.8 g (80% crude yield) of a water-clear, colorless condensate were obtained which, according to GC and GC/MS analyses, comprises, as main components, more than 50% of isomeric 3,4-dimethylcyclotetradecanones (no baseline separation) and about 5% 2-methylcyclotetradecanone (m/e in each case 238), as well as other dehydrogenation and fragmentation products.

Diastereomer mixture (cis/trans compounds), characteristic peaks: $^1$H-NMR (300 MHz, CDCl$_3$): 0.84–0.83 (3 d, J=6.5–7 Hz), 0.78 (d, J=6.6 Hz).$^{13}$C-NMR (75 MHz, CDCl$_3$) 211.6/211.3(s); 49.3, 44.9, 41.8,39.8(4 t); 34.0, 33.3, 32.6, 31.2 (4 q); 32.8 (t); 28.6–24.4 CH$_2$ signals (t) not completely resolved; 16.7, 16.1, 14.8, 13.4 (4 q).EI-MS (GC/MS): Product peaks not completely separated, 238.1/ 238.1 (M$^{+\circ}$).

B. Bicyclic Systems 3.1. (cis/trans)-Bicyclo[10.4.0]hexadecadecan-2-one from 1-(1-cyclohexenyl)cyclododecan-1-ol.

0.5 g of 1-(1-cyclohexenyl)cyclododecan-1-ol (1.9 mmol) was quickly vaporized at 140–170° C. (reactor temperature 690–700° C.). 0.45 g of a slightly yellow-colored oil were obtained as condensate which, according to GC and GC/MS analysis, had as well as others three new mass-isomeric main components with m/e 264 (36, 9 and 12%). Separation of the components by chromatography over silica gel (hexane/ TBME 98:2) was only partially successful and fractions of varying composition were obtained (partial crystallization).

The isolated crystalline fraction revealed two signals in GC in the ratio of about 9:1 (trans/cis isomers).

$^1$H-NMR (300 MHz, CDCl$_3$): 2.82–2.70 (m, 1 H), 2.63–2.56 (m, 1 H), 2.25–2.12 (m, 1 H), 2.08–1.48 (m, 7 H), 1.47–1.0 (m, 22 H). $^{13}$C-NMR (75 MHz, CDCl$_3$) Isomer A (main isomer): 213.2 (s), 52.6 (d), 37.9 (t), 37.0 (d), 28.4, 26.2, 26.0 25.9, 25.5, 25.0, 24.5 (2), 24.4, 24.1, 24.0, 23.5, 21.5, 20.7 (14 t). Isomer B (weak): 215.1 (s), 57.3 (d), 38.7(d).EI-MS(GC/MS): 265.1 (35, M+1), 264.1 (58, M$^{+\circ}$), 246.1 (10), 209 (15), 137 (18), 125 (40), 96 (48), 81 (52), 67 (55), 55 (100).

The oily product produced in the same manner was identified as cyclohexen-1-yl undecyl ketone (about 20%, m/e 264).

C. Unsaturated Systems 4.1. Cyclotetradec-2-enone from 1-ethynylcyclododecanol.

2.1 g of 1-ethynylcyclododecanol (9 mmol) was vaporized at 120–135° C. over the course of about 15 min (reactor temperature 660–670° C.). 1.8 g of condensate were isolated which, according to GC/MS analysis, had, as well as about 10% starting material and about 20% cyclododecanone, two or more components with m/e 208 as molecular ion signal. Column chromatography over silica gel (hexane/TBME 98:2) isolated the UV-active main fraction (0.6 g, 29%) as a colorless oil:

$^1$H-NMR (300 MHz, CDCl$_3$): 6.83 (td, J=15.8, 7.4 Hz, 1 H); 6.20 (dt J=15.8, 1.3 Hz, 1 H); 2.53–2.48 (m, 2 H); 2.30–2.26 (m, 2 H); 1.80–1.67 (m, 2 H), 1.58–1.52 (m, 2H), 1.45–1.2 (m, 14 H). $^{13}$C-NMR (75 MHz, CDCl$_3$): 202.1 (s), 148.2, 130.3 (2 d), 40.4, 31.4, 26.6, 26.3, 26.2, 26.0, 25.8, 25.7, 25.4, 25.0, 24.9 (11 t).EI-MS (GC/MS): 209.1 (5, M+1), 208.1 (15, M$^{+\circ}$), 165 (10), 98 (40), 95 (50), 81 (90), 67 (65), 55 (100).

4.2. Cyclopentadec-2-enone from 1-ethynylcyclotridecanol.

2.0 g of 1-ethynylcyclotridecanol (9 mmol) was vaporized at 125–130° C. over the course of about 15 min (reactor temperature 670–690° C.). 1.8 g of condensate were isolated which, according to GC/MS analysis, had, as well as about 10% starting material and about 15% cyclotridecanone, two or more components with m/e 222 as molecular ion signal. Column chromatography over silica gel (hexane/TBME 98:2) isolated the UV-active main fraction 0.44 g (22%):

$^1$H-NMR (300 MHz, CDCl$_3$): 6.81 (td, J=15.7, 7.5 Hz, 1 H); 6.19 (dt J=15.7, 1.3 Hz, 1 H); 2.52–2.47 (m, 2 H); 2.30–2.23 (m, 2 H); 1.72–1.44 (m, 4H), 1.4–1.2 (m, 16 H). $^{13}$C-NMR (75 MHz, CDCl$_3$): 201.7 (s), 147.9, 130.7 (2 d), 40.0, 31.6, 26.9, 26.8, 26.7, 26.6 (2), 26.5, 26.2, 26.0, 25.4, 25.2 (12 t).EI-MS (GC/MS): 223.1 (5, M+1), 222.1 (15, M$^{+\circ}$), 164 (10), 109 (50), 96 (52), 95 (50), 81 (80), 68 (55), 55 (100).

4.3. (E/Z)-3-Methylcyclopentadec-2-en-1-one from 1-(1-propynyl)cyclotridecanol.

0.8 g of 1-(1-propynyl)cyclododecanol (3.3 mmol) was vaporized at 130–140° C. (reactor temperature 660–670° C.), giving 0.5 g of condensate as a yellowish oil. GC and GC-MS analysis revealed a complex product mixture which comprised, as well as about 12% cyclotridecanone (m/e 196), about 15–20% alkene fractions (m/e 218), inter alia three fractions (about 18, 15, 11%) with mass-someric molecular ion peaks (m/e 236). Using chromatography over silica gel (hexane/TBME 98:2) it was possible, after separating off the alkene fraction, to separate off part of the ketone fraction eluted first (colorless oil):

$^1$H-NMR (300 MHz, CDCl$_3$): 6.09 (br. s, 1H), 2.76 (t, J=6.8 Hz, 2 H), 2.46–2.35 (m, 2 H), 1.86 (d, J=1.3 Hz, 3 H), 1.74–1.2 (m, 20 H. $^1$H-NMR (75 MHz, CDCl$_3$): 201.8 (s), 158.4 (s), 125.0 (d), 41.8 (t), 31.6, 29.3, 27.0, 26.9, 26.8, 26.7, 26.5, 26.3, 26.1, 25.3, (10 t) 25.1 (q), 23.8 (t). EI-MS (GC/MS): 237.1 (5, M+1), 236.0 (18, M$^{+\circ}$), 221.0 (12), 123.0 (13), 109 (46), 98 (87), 95 (100), 83 (90), 67 (52), 55 (80).

The following product fractions not sufficiently separated by column chromatography over silica gel were purified. Catalytic hydrogenation of this mixture with palladium (10%) on activated carbon in ethyl acetate and subsequent renewed column chromatography over silica gel (hexane/ TBME 98:2) gave three main fractions, one of which (0.15 g, 19%) proved to be identical to 3-methylcyclopentadecanone (muscone) by GC, GC/MS analyses and NMR spectroscopy (cf. II.2.2.). The other compounds (content about 10 and 15%) were identified as cyclotridecanone and hexadecan-4-one.

4.4. (E/Z)-3-Methylcyclotetradec-2-en-1-one from 1-(1-propynyl)cyclododecanol.

1.1 g of 1-(1-propynyl)cyclododecanol (5 mmol) was vaporized at 130–140° C. (reactor temperature 660–680° C.), giving 0.9 g of condensate as a yellowish oil. GC and GC-MS analysis revealed a complex product mixture which, as well as about 15% cyclododecanone (m/e 182), had about 15–20% alkene fractions (m/e 204), inter alia three fractions (about 25, 20, 15%) with mass isomeric molecular ion peaks (m/e 222).

$^1$H-NMR spectrum of this mixture: 6.21 (s), 6.09 (s), 2.78 (t, J=6.8 Hz), 2.6–2.35 (m), 2.13 (d, J=1 Hz), 2.02 (s), 1.95–1.15 (m), 0.88 (t, J=6.8 Hz).

Catalytic hydrogenation of this mixture with palladium (10%) over activated carbon in ethyl acetate and subsequent column chromatography over silica gel (hexane/TBME 98:2) gave two main fractions, one of which (0.35 g, 32%) proved to be identical to 3-methylcyclotetradecanone by GC, GC/MS analyses and NMR spectroscopy. The second product (content about 15%) was identified as pentadecan-4-one.

5.1. (R/S)-3-Methylcyclotetradecanone from (E/Z)-1-(trimethyl-silyloxy)-1-(1-propenyl)cyclododecanol and subsequent hydrolysis of the cyclic trimethylsilyl enol ether intermediate:

1.5 g of (E/Z)-1-propen-1-yl-1-trimethylsilyloxycyclododecane (5 mmol, E:Z-isomer ratio according to $^1$H-NMR and GC about 3:2) were vaporized at 120–130° C. within 15 min (reactor temperature 660–670° C.). 1.3 g of condensate (86%) as colorless oil. According to GC/MS analyses, reaction about 90%, were, as well as a total of about 30–40% alkene fractions (desilylation, $M^{+o}$= 206) with about 25 and 15% in each case two new broadened product signal pairs with m/e 296 ($M^{+o}$, trimethylsilyl enol ether isomers) were observed.

EI-MS: 297.2 (5), 296.2 (15, $M^{+o}$), 281.2 (20), 253.1 (10), 197.0 (18), 169.0 (60), 73.0 (100).

The resulting crude condensate was dissolved in 20 ml of THF and, with stirring, treated with a few drops of dilute sulfuric acid and a dilute aqueous potassium fluoride solution. After stirring overnight, the mixture was poured onto water, extracted with hexane, and chromatographed after customary work-up over silica gel (hexane/TBME 97:3). As well as a UV-active prefraction (alkene fraction), 0.42 g (28%) of a colorless oil are obtained, which prove to be identical to the 3-methylcyclo-tetradecanone already prepared previously, by GC, GC/MS analyses and NMR-spectroscopy.

What is claimed is:

1. A method for producing macrocyclic ketones of the formula Ia; or Ib

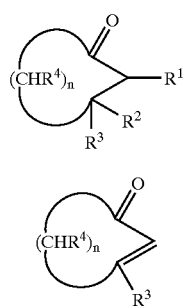

wherein $R^1$, $R^2$, and $R^3$ are independently hydrogen, or a $C_1$ to $C_6$ alkyl group; or $R^1$, $R^2$, and $R^3$ are independently hydrogen, or a $C_1$ to $C_6$ alkyl group, and $R^1$ and $R^2$ or $R^2$ and $R^3$ form together with the carbon atom(s) to which they are attached a ring;

$R^4$ is hydrogen, a linear or branched $C_1$ to $C_4$ alkyl group; and n is an integer of 7 to 14;

comprising the steps:

(a) converting to 100° C.–300° C. into the gas phase a compound of formula IIa or formula IIb

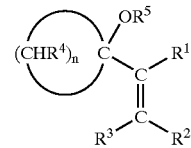

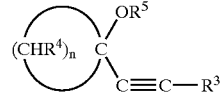

wherein $R^1$, $R^2$, $R^3$, $R^4$, and n have the same meanings as above; and $R^5$ is either hydrogen or a trialkylsilyl group or an alkali metal cation; and (b) heating the compound of formula IIa or formula IIb, converted into the gas phase under (a), to temperatures of from 500° C. to 700° C., and (c) if $R^5$ is a trialkylsilyl group, hydrolysis of the trialkylsilyl ether resulting under (b) into the corresponding ketone of the formula Ia or Ib.

2. The method according to claim 1, wherein $R^1$, $R^2$, and $R^3$ are independently hydrogen or methyl and at least one of $R^1$, $R^2$, and $R^3$ is methyl.

3. The method according to claim 1, wherein the compound of formula IIa or the compound of formula IIb is dissolved in an inert solvent prior to the converted into the gas phase.

4. The method according to claim 1, wherein the compound of formula IIa or the compound of formula IIb is converted into the gas phase continuously.

5. The method according to claim 1, wherein the compound of formula IIa or the compound of formula IIb is converted into the gas phase at 120° C.–250° C.

6. The method according to claim 1, wherein an inert gas is added to the gas phase of (a).

7. The method according to claim 1, wherein the heating temperature of (b) is from 600° C. to 670° C.

8. A compound selected from the group consisting of:
3-methylcycloheptadecanone,
5-methylcycloheptadecanone,
4-ethylcyclotetradecanone, and
3,4-dimethylcyclotetradecanone.

9. A method for producing a compound of formula IIa or a compound of formula IIb

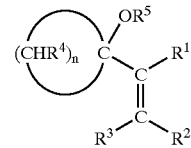

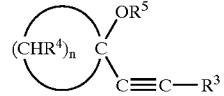

wherein $R^1$, $R^2$, and $R^3$ are independently hydrogen, or a $C_1$ to $C_6$ alkyl group; or $R^1$, $R^2$, and $R^3$ are independently hydrogen, or a $C_1$ to $C_6$ alkyl group, and $R^1$ and $R^2$ or $R^2$ and $R^3$ form together with the carbon atom(s) to which they are attached a ring;

R⁴ is hydrogen, a linear or branched $C_1$ to $C_4$ alkyl group;

n is an integer of 7 to 14; and

R⁵ is hydrogen, a trialkylsilyl group, or an alkali metal cation;

comprising the step of (a) precomplexation of a macrocyclic ketone with an anhydrous Lewis acid at temperatures of from 0° C. to 40° C., and (b) subsequent addition of organometallic alkylene compounds onto the precomplexed macrocyclic ketones under Grignard conditions.

10. A compound selected from the group consisting of: 1-vinyl-1-cycloundecanol, 1-vinyl-1-cyclotridecanol, 1-vinyl-1-cyclotetradecanol, 1-vinyl-1-cyclopentadecanol, (syn/anti)-2-methyl-1-vinyl-1-cyclododecanol, (syn/anti)-2-ethyl-1-vinyl-1-cyclododecanol, (syn/anti)-3-methyl-1-vinyl-1-cyclopentadecanol, (E/Z)-1-(1-propen-1-yl)cyclododecanol, (E/Z)-1-(1-propenyl)cyclotridecanol, (E/Z)-1-(1-propenyl)cyclotetradecanol, (E/Z)-1-(1-propen-1-yl)cyclopentridecanol, 1-(1-methyltethenyl)cycloundecanol, 1-(2-methyl-1-propenyl)cyclododecanol, (E/Z)-1-(2-buten-2-yl)cyclododecanol, (E/Z)-1-(trimethylsilyloxy)-1-(1-propenyl)cyclododecanol), and (E/Z)-2-methyl-1-(1-propen-1-yl)cyclododecanol.

11. A compound selected from the group consisting of 1-ethynylcyclotridecanol, and 1-(1-propynyl)cyclododecanol.

* * * * *

UNITED STATES PATENT AND TRADEMARK OFFICE
CERTIFICATE OF CORRECTION

PATENT NO. : 6,951,964 B2
DATED : October 4, 2005
INVENTOR(S) : Georg Frater et al.

It is certified that error appears in the above-identified patent and that said Letters Patent is hereby corrected as shown below:

Column 20,
Line 40, change "600° C. to 670° C." to -- 500° C. to 670° C. --.

Column 22,
Lines 5-6, change "(E/Z)-1-(1-propen-1-yl)cyclopentridecanol" to
-- (E/Z)-1-(1-propen-1-yl)cyclopentadecanol --.

Signed and Sealed this

Twenty-first Day of March, 2006

JON W. DUDAS
*Director of the United States Patent and Trademark Office*